United States Patent [19]

Rohe et al.

[11] 4,087,272

[45] May 2, 1978

[54] 4-(3-TRIFLUOROMETHYLPHENOXY)-PHENYLUREA COMPOUNDS AND HERBICIDAL COMPOSITIONS

[75] Inventors: Lothar Rohe, Wuppertal; Jürgen Schramm, Dormagen; Erich Klauke, Odenthal; Ludwig Eue, Leverkusen; Robert R. Schmidt, Cologne, all of Germany

[73] Assignee: Bayer Aktiengesellschaft, Leverkusen, Germany

[21] Appl. No.: 710,828

[22] Filed: Aug. 2, 1976

[30] Foreign Application Priority Data

Aug. 27, 1975   Germany .............................. 2538178

[51] Int. Cl.$^2$ ...................... A01N 9/20; C07C 127/19
[52] U.S. Cl. ................................... 71/120; 260/553 A
[58] Field of Search ...................... 260/553 A; 71/120

[56] References Cited

U.S. PATENT DOCUMENTS

| 3,060,235 | 10/1962 | Martin et al. ..................... 260/553 A |
| 3,901,687 | 8/1975 | Bailey ..................... 71/120 |

FOREIGN PATENT DOCUMENTS 2,411,320   9/1975   Germany ............................... 71/120

OTHER PUBLICATIONS

Rohr, C. A., 71 (1969) 123897 w.

Primary Examiner—J. P. Brust
Attorney, Agent, or Firm—Burgess, Dinklage & Sprung

[57] ABSTRACT

4-(3-Trifluoromethylphenoxy)-phenylurea compounds of the formula

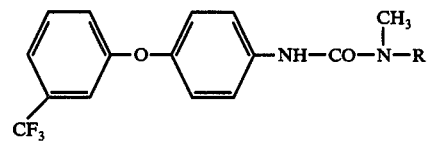

wherein R is hydrogen or methyl, exhibit powerful herbicidal properties.

10 Claims, No Drawings

4-(3-TRIFLUOROMETHYLPHENOXY)-PHENYLUREA COMPOUNDS AND HERBICIDAL COMPOSITIONS

The present invention relates to certain new 4-(3-trifluoromethylphenoxy)-phenylurea compounds, and to herbicidal compositions and methods employing such compounds.

It is known that N,N-dimethyl-N'-(3-trifluoromethyl-4-phenoxy)-phenylurea can be used for combating weeds from German Offenlegungsschrift (German Published Specification) No. 1,901,501. However, this compound is not adequately active against all weeds, especially if low amounts and low concentrations are used. Thus, for example, its activity against weeds such as Echinochloa and Urtica is low.

The present invention provides, as new compounds, the 4-(3-trifluoromethylphenoxy)-phenylureas of the general formula

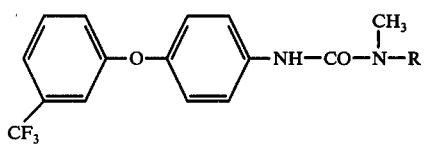

in which
R is hydrogen or methyl.

The compounds of this invention have been found to exhibit powerful herbicidal properties.

Surprisingly, the 4-(3-trifluoromethylphenoxy)-ureas according to the invention exhibit a greater herbicidal action than N,N-dimethyl-N'-(3-trifluoromethyl-4-phenoxy)-phenylurea, known from the state of the art. The compounds according to the invention are particularly suitable for combating weeds when used by the post-emergence process. Their activity is distinctly superior to that of N,N-dimethyl-N'-(3-trifluoromethyl-4-phenoxy)-phenylurea against weeds such as, for example, Echinochloa and Urtica. The compounds according to the invention thus represent a valuable enrichment of the art.

The present invention also provides a process for the preparation of a 4-(3-trifluoromethyl-phenoxy)-phenylurea of the formula (I) in which (a) 4-(3-trifluoromethylphenoxy)-aniline of the formula

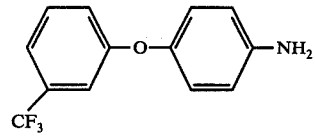

is reacted with phosgene and subsequently, if appropriate without intermediate isolation of the resulting isocyanate, with an amine of the general formula

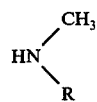

in which
R has the above-mentioned meaning,
if appropriate in the presence of a diluent, or (b), provided that the compound of the formula (I) in which R represents methyl is required, 4-(3-trifluoromethylphenoxy)-aniline of the formula (II) is reacted with N,N-dimethylcarbamic acid chloride of the formula

if appropriate in the presence of an acid acceptor and, if appropriate, in the presence of a diluent, or (c), provided that the compound of the formula (I) in which R represents hydrogen is required, 4,-(3-trifluoromethylphenoxy)-aniline of the formula (II) is reacted with methyl isocyanate of the formula

if appropriate in the presence of a diluent and if appropriate in the presence of a catalytic amount of a base.

If 4-(3-trifluoromethylphenoxy)-aniline, phosgene and dimethylamine are used as starting materials, the course of the reaction according to process variant (a) can be represented by the following equation:

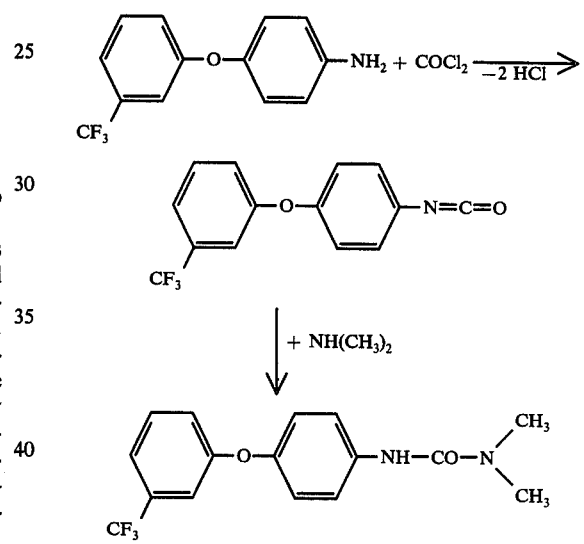

If 4-(3-trifluoromethylphenoxy)-aniline and N,N-dimethylcarbamic acid chloride are used as starting materials, the course of the reaction according to process variant (b) can be represented by the following equation:

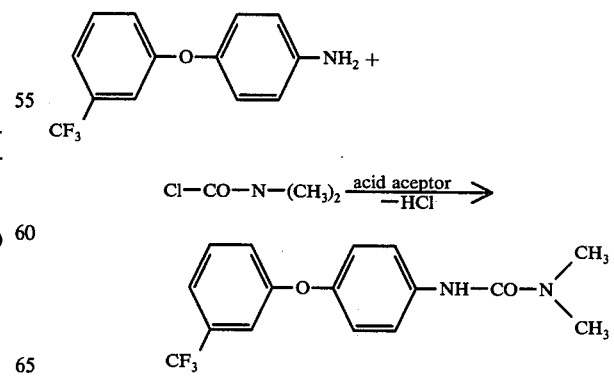

If 4-(3-trifluoromethylphenoxy)-aniline and methyl isocyanate are used as starting materials, the course of the reaction according to process variant (c) can be represented by the following equation:

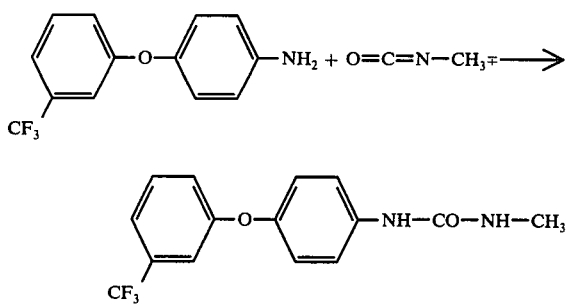

4-(3-Trifluoromethylphenoxy)-aniline, used as the starting material in carrying out the process variants (a), (b) and (c), was not previously known but can be prepared in a simple manner in accordance with generally customary methods, which are described in the literature.

For example, 4-(3-trifluoromethylphenoxy)-aniline is obtained by hydrogenating 4-(3-trifluoromethylphenoxy)-nitrobenzene in the presence of a catalyst, such as, for example, Raney nickel, and in the presence of an inert solvent, such as, for example, ethanol, at a temperature of 40° C and under a hydrogen pressure of 60 atmospheres. 4-(3-Trifluoromethylphenoxy)-nitrobenzene required as the starting material, can be obtained by converting 3-aminobenzotrifluoride, by diazotization and boiling, into 3-hydroxybenzotrifluoride, and reacting the latter with 4-nitrochlorobenzene in the presence of a base, such as, for example, potassium hydroxide solution. However, it is also possible to prepare 4-(3-trifluoromethylphenoxy)-nitrobenzene by nitration of 3-trifluoromethyldiphenyl ether with a mixture of nitric acid and sulfuric acid (see the preparative Examples hereinafter).

The amines used as further starting materials in carrying out process variant (a) are known, as in phosgene, and can be prepared in accordance with customary methods, also on an industrial scale.

N,N-Dimethyl-carbamic acid chloride, required as a starting material in process variant (b) is already known, as is methyl isocyanate, which is required as a starting material in process variant (c) according to the invention.

The process variants (a), (b) and (c) according to the invention are each preferably carried out in the presence of a diluent. Practically all inert organic solvents can be used for this purpose, especially aliphatic and aromatic hydrocarbons, such as petroleum ether, benzine, benzene, toluene and xylene; chlorinated aliphatic and aromatic hydrocarbons, such as methylene chloride, chloroform, carbon tetrachloride, ethylene chloride and chlorobenzene; ethers, such as diethyl ether, dibutyl ether, tetrahydrofuran and dioxan; ketones, such as acetone, methyl ethyl ketone, methyl isopropyl ketone and methyl isobutyl ketone; nitriles, such as acetonitrile and propionitrile; and amines such as pyridine.

As acid acceptors, all customary acid-binding agents can be used in process variant (b) according to the invention. Especially suitable are alkali metal carbonates, such as sodium carbonate and potassium carbonate, as well as alkali metal alcoholates, such as sodium methylate and sodium ethylate, and also aliphatic, aromatic or heterocyclic amines, such as, for example, triethylamine, dimethylamine, dimethylaniline, dimethylbenzylamine and pyridine.

Process variant (c) according to the invention is preferably carried out in the presence of a catalytic amount of a base. As bases it is possible to use for this purpose those which have already been mentioned as being preferred in the context of process variant (b). Triethylamine may be mentioned as a specific example.

In the reactions according to process variant (a), (b) and (c), the reaction temperatures can be varied within a fairly wide range. Process variant (a) is in general carried out at temperatures between −10° and +150° C, preferably between −5° and +130° C. Process variant (b) is in general carried out at temperatures between −10° and +150° C, preferably between 0° and 80° C. Process (c) is generally carried out at temperatures between −10° and +150° C, preferably between 0° and 40° C.

In a preferred mode of carrying out process variant (a), the 4-(3-trifluoromethylphenoxy)-aniline of the formula (II) is first reacted with an excess of phosgene; thereafter, when the reaction has ended, dry nitrogen is passed over the reaction mixture to remove excess phosgene, and then a sufficiently large excess of amine of the formula (III) is added that the reaction mixture gives a basis reaction. The reaction products are isolated in accordance with customary methods. For example, the procedure followed may be that after completion of the reaction any solvent present, as well as amine present in excess, is substantially removed, and the residue which remains is recrystallized.

In a preferred mode of carrying out process variant (b), 1.2 to 1.5 moles, preferably 1.4 moles, of N,N-dimethylcarbamic acid chloride and, if appropriate, an excess of an acid acceptor, are employed per mole of 4-(3-trifluoromethylphenoxy)-aniline of the formula (II). The reaction product is isolated in accordance with the customary methods.

In a preferred mode of carrying out process variant (c), 1.2 to 1.4 moles, preferably 1.3 moles, of methyl isocyanate of the formula (V) and, if appropriate, a catalytic amount of an acid acceptor, are employed per mole of 4-(3-trifluoromethylphenoxy)-aniline of the formula (II). The reaction product is isolated in accordance with customary methods. In general, the procedure followed is that after completion of the reaction any solvent which may be present is partially stripped off and the product which crystallizes out from the residue is filtered off.

The process for making the compounds of the present invention is illustrated in the following preparative Examples.

EXAMPLE 1

Process variant (a)

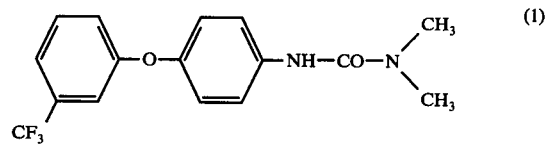

Phosgene was passed into a solution of 25.3 g (0.1 mole) of 4-(3-trifluoromethylphenoxy)-aniline in 200 ml of chlorobenzene for 1 hour at −5° C. The reaction mixture was then warmed slowly and the introduction of phosgene at 120° C was repeated until the reaction mixture became a clear solution.

Dry nitrogen was then passed over the reaction mixture for half an hour to remove excess phosgene. Dimethylamine was then introduced at 0° C until the reaction mixture showed a basic reaction. After stirring for one hour at room temperature, the bulk of the chlorobenzene was distilled off and the residue was recrystallized from a little acetonitrile. 25 g (77% of theory) of N,N-dimethyl-N'-[4-(3-trifluoromethylphenxoy)-phenyl]-urea were obtained in the form of white crystals of melting point 129°-131° C.

EXAMPLE 2

Process variant (c)

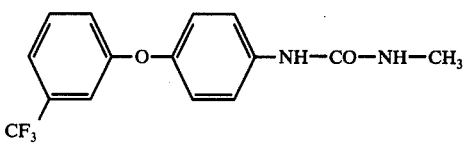

25.3 g (0.1 mole) of 4-(3-trifluoromethylphenoxy)-aniline were dissilved in 100 ml of acetonitrile and 3 drops of triethylamine and 7.4 g (0.13 mole) of methyl isocyanate were added at 10° C. The mixture was stirred for a further 4 hours at room temperature. A part of the solvent was then stripped off. 23 g (74% of theory) of N-methyl-N'[4-(3-trifluoromethylphenoxy)-phenyl]-urea, of melting point 160° C. crystallized out from the residue.

Preparation of the starting materials

EXAMPLE I

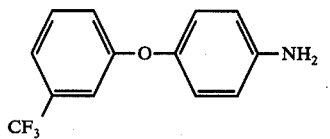

184 g (0.65 mole) of 4-(3-trifluormethylphenoxy)-1-nitrobenzene were dissolved in 1.2 l of ethanol and hydrogenated with 30 g of Raney nickel as the catalyst at 40° C and 60 atmospheres gauge hydrogen pressure. After separating off the catalyst, the solvent was stripped in vacuo and the residue was distilled. After a small amount of first runnings, the main component distilled at 121°-124° C and 0.3 mm Hg.

142 g (86.5% of theory) of 4-(3-trifuloromethylphenoxy)-aniline of refractive index $N_D^{20} = 1.5472$ were obtained.

EXAMPLE II

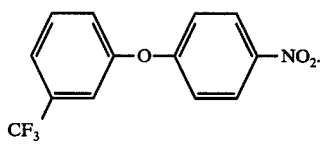

Variant α

88.5 g (0.5 mole) of 3-aminobenzotrifluoride were allowed to run into a slution of 2 l of water and 73.5 g (0.75 mole) of sulfuric acid at 10° C, the mixture was then cooled rapidly and a solution of 35 g (0.5 mole) of sodium nitrate in 100 ml of water was added in the course of one hour at 0° to 5° C. The mixture was stirred further for half an hour at −10° C and half an hour at room temperature and was then slowly heated up.

At 80° to 90° C, a vigorous evolution of nitrogen was observable. Towards the end, the mixture was further warmed to 100° C. The dark red oil which separated out was taken up in 350 ml of methylene chloride and the aqueous phase was separated off and discarded. After stripping off the solvent, the residue was distilled. 34.7 g (43% of theory) of 3-hydroxybenzotrifluoride of boiling point 72° to 90° at 12 mm Hg were thus obtained.

A solution of 55 g of potassium hydroxide in 50 ml of water and 136 g (0.84 mole) of 3-hydroxybenzotrifluoride were introduced into 500 ml of dimethylsulfoxide. Thereafter, about 250 ml of dimethylsulfoxide were distilled off and a solution of 132 g (0.84 mole) of 4-nitrochlorobenzene in 150 ml of dimethylsulfoxide was then added dropwise at 70° C. The mixture was stirred for a further 2 hours at 100° C and 1 hour at 120° C. The product was then precipitated by adding methanol and ice, and was filtered off. After recrystallizing the moist product from ethanol, 200 g (84% of theory) of 4-(3-trifluoromethylphenoxy)-nitrobenzene of melting point 57°-85° C were obtained.

Variant β

765 g of 3-trifluoromethyldiphenyl ether (prepared according to U.S. Pat. No. 2,464,877) in 200 ml of acetic anhydride were nitrated at a temperature of 0°-5° C by adding a mixture of 312 g of nitric acid (65% strength) and 528 ml of sulfuric acid. The reaction mixture was stirred for a further 2 hours at this temperature. 3 l of methylene chloride and 3 l of ice-water were then added and the organic phase was separated off and washed twice with 5% strength sodium hydroxide solution and once with water. The solvent was then stripped off and the residue was distilled in vacuo. 700 g of a fraction with a boiling point of 135°-140° C at 0.5 mm Hg, and a refractive index $n_D^{20}$ of 1.5507, were obtained. On freezing-out, 560 g of crystals of melting point 51°-54° C were obtained. On recrystallizing the frozen-out product once from ethanol, 3-trifluormethyl-4'-nitrodiphenyl ether of melting point 57°-58°, and having a purity of 99% according to a gas chromatogram, was obtained.

The active compounds according to the invention influence plant growth and can therefore be used as defoliants, desiccants, agents for destroying broad-leaved plants, germination inhibitors and, especially, weed-killers. Weeds, in the broadest sense, are to be understood as all plants which grow in locations where they are undesired. Whether the compounds according to the invention act as total herbicides or as selective herbicides depends essentially on the amount used.

The active compounds according to the invention can be used, for example, in connection with the following plants:

Dicotyledon weeds such as mustard (Sinapis), cress (Lepidium), bed straw (Galium), chickweed (Stellaria), camomile (Matricaria), mayweed (Anthemis), gallant soldier (Galinsoga), goosefoot (Chenopodium), annual nettle (Urtica), groundsel (Senecio), pigweed (Amaranthus), purslane (Portulaca), cocklebur (Xanthium), bindweed (Convolvulus), morning glory (Ipomoea), knotweed (Polygonum), sesbania (Sesbania), ragweed (Ambrosia), spear thistle (Cirsium), common thistle (Carduus), sow thistle (Sonchus), nightshade (Solanum), field cress (Rorippa), toothcup (Rotala), (Lindernia), deadnettle (Lamium), speedwell (Veronica), mallow (Abutilon), emex (Emex), thornapple (Datura), violet (Viola), hemp-nettle (Galeopsis), poppy (Papaver) and knapweed (Centaurea);

Dicotyledon cultures such as cotton (Gossypium), soya bean (Glycine), beet (Beta), carrot (Daucus), bean (Phaseolus), pea (Pisum), potato (Solanum), flax (Linum), morning glory (Ipomoea), broad bean (Vicia), tobacco (Nicotiana), tomato (Lycopersicon), groundnut (Arachis), cabbage (Brassica), lettuce (Lactuca), cucumber (Cucumis) and marrow (Cuburbita);

Monocotyledon weeds such as barnyard grass (Echinochloa), foxtail (Setaria), wild millet (Panicum), crabgrass (Digitaria), timothy (Phleum), bluegrass (Poa), fescue (Festuca), goosegrass (Eleusine), signalgrass (Brachiaria), ryegrass (Lolium), cheat (Bromus), oats (Avena), flatsedge (Cyperus), sorghum (Sorghum), quackgrass (Agropyron), Bermuda grass (Cynodon), Monocharia, fimbristylis (Fimbristylis), arrowhead (Sagittaria), spikerush (Eleocharis), bulrush (Scirpus), paspalum (Paspalum), Ischaemum, gooseweed (Sphenoclea), crowfoot grass (Dactyloctenium), redtop (Agrostis), meadow foxtail (Alopecurus) and silky bent-grass (Apera);

Monocotyledon cultures such as rice (Oryzae), maize (Zea), wheat (Triticum), barley (Hordeum), oats (Avena), rye (Secale), sorghum (Sorghum), millet (Panicum), sugar cane (Saccharum), pineapple (Ananas), asparagus (Asparagus) and onion (Allium).

The use of the active compounds according to the invention is, however, in no way restricted to the genera indicated above, but extends, in the same way, also to other plants.

Depending on the concentration, the compounds are suitable for the total combating of weeds, for example on industrial terrain and rail tracks, and on paths and squares which may or may not be planted with trees. Equally, the compounds can be employed for combating weeds in permanent cultures, for example afforestation, decorative tree plants, orchards, vineyards, citrus groves, nut orchards, banana plantations, coffee plantations, tea plantations, rubber plantations, oil palm plantations, cacao plantations, soft fruit orchards and hopfields, and for the selective combating of weeds in annual crops.

The active compounds according to the present invention can be converted into the usual formulations, such as solutions, emulsions, suspensions, powders, pastes and granulates. These may be produced in known manner, for example by mixing the active compounds with extenders, that is, liquid or solid or liquefied gaseous diluents or carriers, optionally with the use of surface-active agents, that is emulsifying agents and/or dispersing agents and/or foamforming agents. In the case of the use of water as an extender, organic solvents can, for example, also be used as auxiliary solvents.

As liquid diluents or carriers, there are preferably used aromatic hydrocarbons, such as xylenes, toluene, benzene or alkyl naphthalenes, chlorinated aromatic or aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethyl formamide, dimethyl sufoxide or acetonitrile, as well as water.

By liquefied gaseous diluents or carriers are meant liquids which would be gaseous at normal temperatures and pressures, for example aerosol propellants, such as halogenated hydrocarbons, for example freon.

As solid diluents or carriers, there are preferably used ground natural minerals, such as kaoline, clays, talc, chalk, quartz, attapulgite, montmorillonite or diatomaceous earth, or ground synthetic minerals, such as highly-dispersed silicic acid, alumina or silicates.

Preferred examples of emulsifying and foam-forming agents include non-ionic and anionic emulsifiers, such as polyoxyethylene-fatty acid esters, polyoxyethylene-fatty alcohol ethers, for example alkylarylpolyglycol ethers, alkyl sulfonates, alkyl sulfates and aryl sulfonates as well as albumin hydrolyzation products; and preferred examples of dispersing agents include lignin sulfite waste liquors and methyl cellulose.

The active compounds according to the invention, as such or as their formulations, can be combined with other herbicidally active compounds in order to boost and supplement their spectrum of action, depending on the intended use; ready-mixed formulations, or tank mixing, may be employed. In particular, the active compounds mentioned below and other representatives of the groups of active compounds characterized by these particular active compounds are suitable for this purpose.

2,3,6-Trichlorobenzoic acid and its salts, 2,3,5,6-tetrachlorobenzoic acid and its salts, 3-nitro-2,5-dichlorobenzoic acid and its salts, 3-amino-2,5-dichlorobenzoic acid and its salts, 2-methoxy-3,6-dichlorobenzoic acid and its salts, 2-methoxy-3,5,6-trichlorobenzoic acid and its salts, 2,6-dichloro-thiobenzamide, 2,6-dichlorobenzonitrile, 2,4-dichlorophenoxyacetic acid as well as its salts and esters, 2,4,5-trichlorophenoxyacetic acid and its salts and esters, (2-methyl-4-chlorophenoxy)-acetic acid and its salts and esters, 2-(2,4-dichlorophenoxy)-propionic acid, 2-(2-methyl-4-chloro-phenoxy)-propionic acid and 2-(2,4,5-trichlorophenoxy)-propionic acid and their salts and esters, 4-(2,4-dichlorophenoxy)-butyric acid and its salts and esters, 4-(2-methyl-4-chlorophenoxy)-butyric acid and its salts and esters, 2,3,6-trichlorophenyl-acetic acid and its salts and 4-amino-3,5,6-trichloropicolinic acid.

Trichloroacetic acid and its salts, 2,2-dichloropropionic acid and its salts, 2-chloro-N,N-diallylacetic acid amide, dinitrocresol, dinitro-sec.-butylphenol and its salts.

3-Phenyl-1,1-dimethyl-urea, 3-(4'-chlorophenyl)-1,1-dimethyl-urea, 3-(3',4'-dichlorophenyl)-1,1-dimethyl-urea, 3-(3',4'-dichlorophenyl)1-n-butyl-1-methyl-urea, 3-(3',4'-dichlorophenyl)-1,1,3-trimethyl-urea, 2-(4'-chlorophenyl)-1-methoxy-1-methyl-urea, 3-(3'trifluoromethyl-phenyl)-1,1-dimethyl-urea, 3-(3',4'-dichlorophenyl)-1-methoxy-1-methyl-urea, 3-(4'bromophenyl)-1-methoxy-1-methyl-urea, 3-(3',4'-dichlorophenyl)-3-methoxy-1,1-dimethyl-urea, 3-(4'-chlorophenoxyphenyl)-1,1-dimethyl-urea, N'-cycloctyl-N,N-dimethyl-urea, 3-(benzthiazol-2-yl)-1,3-dimethyl-urea and 3-(3-chloro-4-methylphenyl)-1,1-dimethyl-urea.

N,N-Di-(n-propyl)-S-n-propyl-thiocarbamic acid ester, N-ethyl-N-(n-butyl)-S-n-propyl-thiocarbamic acid ester, N,N-di-(n-propyl)-S-ethyl-thiocarbamic acid ester, N-phenyl-O-isopropyl-carbamic acid ester, N-(m-chlorophenyl)-O-isopropylcarbamic acid ester, N-(3',4'- dichlorophenyl)-O-methyl-carbamic acid ester, N-(m-chlorophenyl)-O-(4-chloro-butin-(2)-yl)-carbamic acid ester, N-(3'-methylphenyl)-O-(3-methoxycarbonylaminophenyl)-carbamic acid ester and N,N-diisopropyl-thiocarbamic acid 2,3,3-trichloroallyl ester.

3-Cyclohexyl-5,6-trimethylene-uracil, 5-bromo-3-sec.-butyl-6-methyl-uracil, 3,6-dioxo-1,2,3,6-tetrahydropyridazine and 4-amino-5-chloro-1-phenyl-6-pyridazone.

2-Chloro-4-ethylamino-6-isopropylamino-s-triazine, 2-chloro-4,6-bis-(methoxypropylamino)-s-triazine, 2-methoxy-4,6-bis-(isopropylamino)-s-triazine, 2-diethylamino-4-isopropylacetamido-6-methoxy-s-triazine, 2-isopropylamino-4-methoxy-propylamino-6-methylthio-s-triazine, 2-methylthio-4,6-bis-(isopropylamino)-s-triazine, 2-chloro-4,6-bis-(ethylamino)-s-triazine, 2-methylthio-4,6-bis-(ethylamino)-s-triazine, 2-methoxy-4-ethylamino-6-isopropylamino-s-triazine, 2-methylthio-4-ethylamino-6-isopropylamino-s-triazine, 2-methoxy-4,6-bis-(ethylamino)-s-triazine and 2-chloro-4,6-bis-(isopropylamino)-s-triazine.

N,N-Diethyl-2,4-dinitro-6-trifluoromethyl-1,3-phenylenediamine, N,N-di-n-propyl-2,6-dinitro-4-trifluoromethyl-aniline, 4'-nitro-2,4-dichloro-diphenyl ether, 3,4-dichlorophenyl-propionamide and 2',6'-diethyl-N-(methoxymethyl)-2-chloroacetanilide.

The active compounds according to the invention can be present in the formulations as a mixture with other active compounds, such as fungicides, insecticides and acaricides.

The formulations in general contain from 0.1 to 95 percent by weight of active compound, prefering from 0.5 to 90 percent by weight.

The active compounds can be used as such, in the form of their formulations or as the use forms prepared therefrom, such as ready-to-use solutions, emulsions, suspensions, powders, pastes and granules. They may be used in the customary manner, for example by spraying, atomizing, dusting, scattering and watering.

Preferably, they are used in accordance with the post-emergence process.

The amount of active compound employed can vary within fairly wide ranges; it depends essentially on the nature of the desired effect. In general, the amounts used are from 0.1 to 20 kg of active compound per hectare, preferably from 0.2 to 15 kg/ha.

The present invention also provides a herbicidal composition containing as active ingredient a compound of the present invention in admixture with a solid or liquefied gaseous diluent or carrier or in admixture with a liquid diluent or carrier containing a surface-active agent.

The present invention also provides a method of combating weeds which comprises applying to the weeds or a weed habitat a compound of the present invention alone or in the form of a composition containing as active ingredient a compound of the present invention in admixture with a diluent or carrier.

The present invention further provides means of yielding crops protected from damage by weeds by being grown in areas in which immediately prior to and/or during the time of the growing a compound of the present invention was applied alone or in admixture with a diluent or carrier. It will be seen that the usual methods of providing a harvested crop may be improved by the present invention.

The example which follows is intended to illustrate the good herbicidal activity of the active compounds according to the invention.

EXAMPLE A

Post-emergence test

Solvent: 5 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was then diluted with water to the desired concentrations.

Test plants which had a height of 5–15 cm were sprayed with the preparation of the active compound in such a way as to apply the amounts of active compound per unit area which are indicated in the table. The concentration of the spray liquor was so chosen that the amounts of active compound shown in the table were applied in 2,000 l of water/ha. After three weeks, the degree of damage to the plants was rated in % damage in comparison to the development of the untreated control. The figures denote:

0% = no action (like untreated control)
100% = total destruction.

The active compounds, the amounts applied and the results can be seen from the table which follows:

Table A

Post-emergence Test

| Active compound | Amount of active compound used kg/ha | Echinochloa | Chenopodium | Sinopis | Galinsoga | Stellaria | Urtica | Matricaria | Daucus | Oats | Cotton | Wheat |
|---|---|---|---|---|---|---|---|---|---|---|---|---|
| 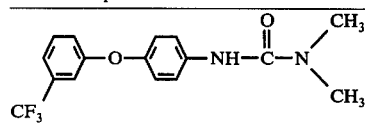 (1) | 2<br>1 | 100<br>100 | 100<br>100 | 100<br>100 | 100<br>100 | 100<br>100 | 100<br>100 | 100<br>100 | 100<br>90 | 80<br>80 | 80<br>80 | 100<br>100 |
| 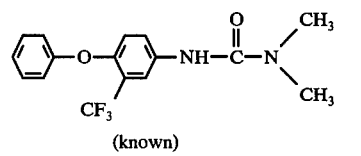 (known) | 2<br>1 | 40<br>40 | 40<br>40 | 100<br>100 | 60<br>40 | 20<br>20 | 40<br>20 | 0<br>0 | 0<br>0 | 0<br>0 | 40<br>0 | 40<br>0 |

What is claimed is:

1. 4-(-Trifluormethylphenoxy)-phenylurea compound of the formula

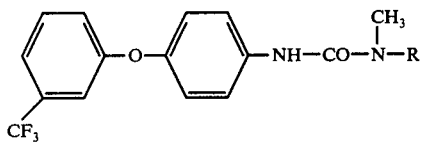

in which
R is hydrogen or methyl.

2. 4-(3-Trifluoromethylphenoxy)-phenylurea compound as claimed in claim 1 designated N,N-dimethyl-N'-[4-(3-trifluoromethylphenoxy)-phenyl]-urea.

3. 4-(3-Trifluoromethylphenoxy)-phenylurea compound as claimed in claim 1 designated N-methyl-N'[4-(3-trifluoromethylphenoxy)-phenyl]-urea.

4. Herbicidal composition comprising a herbicidally acceptable carrier and as an active ingredient a 4-(3-trifluoromethylphenoxy)-phenylurea compound as claimed in claim 1.

5. Method of combating undesired vegetation which method comprises applying to such vegetation or its habitat, in post-emergence treatment, herbicidally effective amounts of a 4-(3-trifluoromethylphenoxy)-phenylurea compound of the formula

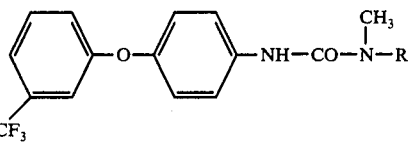

in which
R is hydrogen or methyl.

6. Method as claimed in claim 5 wherein said compound is N,N-dimethyl-N'-[4-(3-trifluoromethylphenoxy)-phenyl]-urea.

7. Method as claimed in claim 5 wherein said compound is N-methyl-N'-[4-(3-trifluoromethylphenoxy)-phenyl]-urea.

8. Method as claimed in claim 5 wherein said compound is applied in an area of cultivation to selectively combat weeds growing therein.

9. Method as claimed in claim 5 wherein the active compound is applied to an area of agriculture in an amount of 0.1 to 20 kg per hectare.

10. Method as claimed in claim 9 wherein the active compound is applied to an area of agriculture in an amount of 0.2 to 15 kg per hectare.